(12) United States Patent
Cadwalader et al.

(10) Patent No.: US 9,271,685 B1
(45) Date of Patent: Mar. 1, 2016

(54) RADIATION SHIELD

(71) Applicant: Worldwide Innovations & Technologies, Inc., Kansas City, KS (US)

(72) Inventors: John A. Cadwalader, Overland Park, KS (US); William P. Radtke, Overland Park, KS (US)

(73) Assignee: Worldwide Innovations & Technologies, Inc., Kansas City, KS (US)

( * ) Notice: Subject to any disclaimer, the term of this patent is extended or adjusted under 35 U.S.C. 154(b) by 0 days.

(21) Appl. No.: 14/455,593

(22) Filed: Aug. 8, 2014

(51) Int. Cl.
*A61B 6/00* (2006.01)
*A61B 6/10* (2006.01)
*G21F 1/08* (2006.01)

(52) U.S. Cl.
CPC .............. *A61B 6/107* (2013.01); *G21F 1/085* (2013.01)

(58) Field of Classification Search
USPC .......... 250/505.1, 515.1, 516.1, 517.1, 518.1, 250/519.1
See application file for complete search history.

(56) References Cited

U.S. PATENT DOCUMENTS

| | | | |
|---|---|---|---|
| 4,938,233 A | 7/1990 | Orrison, Jr. | |
| 6,325,538 B1 | 12/2001 | Heesch | |
| 6,674,087 B2 | 1/2004 | Cadwalader et al. | |
| 7,465,947 B2 | 12/2008 | Magram | |
| 7,763,459 B2 | 7/2010 | Padmini et al. | |
| 8,092,370 B2 | 1/2012 | Roberts et al. | |
| 2010/0084586 A1* | 4/2010 | Teodorescu ............... | G21F 3/00 250/516.1 |

* cited by examiner

*Primary Examiner* — Nicole Ippolito
(74) *Attorney, Agent, or Firm* — Foley & Lardner LLP

(57) ABSTRACT

A radiation attenuation system is provided. The radiation attenuation system includes a first shield panel formed of a first radiation attenuating material, a second shield panel formed of a second radiation attenuating material, and a frame disposed below the first shield panel and the second shield panel. The frame includes a first end portion defining a first array of slots and a second end portion defining a second array of slots. The first array of slots and the second array of slots are configured to receive the first shield panel and the second shield panel such that the second shield panel is spaced apart from the first shield panel to form a first trough sized to fit a limb of a patient.

20 Claims, 2 Drawing Sheets

RADIATION SHIELD

BACKGROUND

The present disclosure relates generally to systems for and methods of attenuating radiation. More particularly, the present disclosure relates to systems for and methods of attenuating radiation during a radiological examination of a patient.

Radiation barriers or shields are used to attenuate (e.g., deflect, absorb, etc.) the flux of electromagnetic radiation originating from a radiation source and directed towards a patient. Radiation can have beneficial and/or negative effects. One beneficial effect of radiation relates to radiological examinations. For purposes of this disclosure, the phrase radiological examination refers generally to any procedure wherein radiation is applied to a patient for the purpose of producing an image or representation of the patient. Radiological examinations may provide a non-invasive means capable of obtaining an image of the internal composition of the patient. Radiological examinations may be employed in a variety of applications including, but not limited to, medical procedures.

During a radiological examination, medical personnel (e.g., technicians, assistants, nurses, physicians, surgeons, etc.) are often positioned near the patient undergoing the procedure. Medical personnel positioned near the patient during the procedure are susceptible to both primary beam radiation and scatter radiation. Scatter radiation is a secondary radiation generated when the primary radiation interacts with the object being impinged. Scatter radiation typically has a frequency range lower than the primary radiation beam and generally moves in a variety of uncontrollable (e.g., random, pseudo-random, etc.) directions. Scatter radiation, like primary radiation, can cause damage to living tissue.

During a radiographic imaging procedure, the primary radiation beam is likely to scatter after impinging the patient mass. Conventional radiation attenuating safeguards, such as table drapes or standard patient shields used during conventional radiographic imaging procedures, may not provide the medical personnel with a desired level of protection from the scatter radiation. Thus, there is a need for an improved radiation attenuation system for and method of shielding an object from primary beam radiation during radiographic imaging of the object. There is also a need for a radiation attenuation system that is configured to shield persons positioned near an object undergoing radiographic imaging from primary beam radiation. There is further a need for a radiation attenuation system that is configured to shield an object or persons positioned near the object undergoing radiographic imaging from scatter radiation.

SUMMARY

One embodiment of the invention relates to a radiation attenuation system. The radiation attenuation system includes a first shield panel formed of a first radiation attenuating material, a second shield panel formed of a second radiation attenuating material, and a frame disposed below the first shield panel and the second shield panel. The frame includes a first end portion defining a first array of slots and a second end portion defining a second array of slots. The first array of slots and the second array of slots are configured to receive the first shield panel and the second shield panel such that the second shield panel is spaced apart from the first shield panel to form a first trough sized to fit a limb of a patient.

Another embodiment relates to a radiation attenuation system for the scanning of a leg of a patient. The radiation attenuation system includes a first shield panel, a second shield panel, a third shield panel, and a frame disposed below the first shield panel, the second shield panel, and the third shield panel. The frame includes a connecting portion extending from a first end to a second end, at least one first arm defining a first array of slots and extending outward from the connecting portion between the first end and the second end, and at least one second arm defining a second array of slots and extending outward from the connecting portion between the at least one first arm and the second end. The first array of slots and the second array of slots are configured to receive the first shield panel, the second shield panel, and the third shield panel such that the second shield panel and the third shield panel are spaced apart from the first shield panel to form a pair of troughs sized to fit the legs of the patient.

Another embodiment relates to an apparatus for attenuating radiation scattered from a patient undergoing radiological examination on a table. The apparatus includes a frame configured to be supported by the table, and a first shield panel formed of a radiation attenuating material and supported by a first portion of the frame. The first shield panel at least partly defines a trough configured to receive a limb of the patient and attenuates radiation scattered from the patient.

Another embodiment relates to a method of attenuating radiation during a radiological examination of a patient. The method includes the steps of providing a frame configured to be supported by a platform; providing a first radiation attenuation plate and a second radiation attenuation plate; receiving on the frame a limb of the patient; receiving by the frame the first radiation attenuation plate along on a first side of the limb of the patient; receiving by the frame the second radiation attenuation plate along on a second side of the limb of the patient, opposite the first radiation attenuation plate; and attenuating radiation directed at the limb of the patient in a direction parallel to the first radiation attenuation plate and the second radiation attenuation plate. The frame may receive the first radiation attenuation plate and the second radiation attenuation plate in slots formed in the frame such that the plates are removably coupled to the frame. The frame may receive the limb of the patient such that the limb is supported by the platform. The limb of the patient may be a leg. The method may include the steps of receiving on the frame a second limb of the patient such that the first radiation attenuation plate is positioned between the limbs of the patient; providing a third radiation attenuation plate; and receiving by the frame the third radiation attenuation plate along on a side of the second limb of the patient, opposite the first radiation attenuation plate. The method may include the steps of receiving by the frame a sheet disposed between the limb of the patient and the frame.

The foregoing is a summary and thus, by necessity, contains simplifications, generalizations, and omissions of detail. Consequently, those skilled in the art will appreciate that the summary is illustrative only and is not intended to be in any way limiting. Other aspects, inventive features, and advantages of the devices and/or processes described herein will become apparent in the detailed description set forth herein and taken in conjunction with the accompanying drawings.

DETAILED DESCRIPTION

Figure 1:
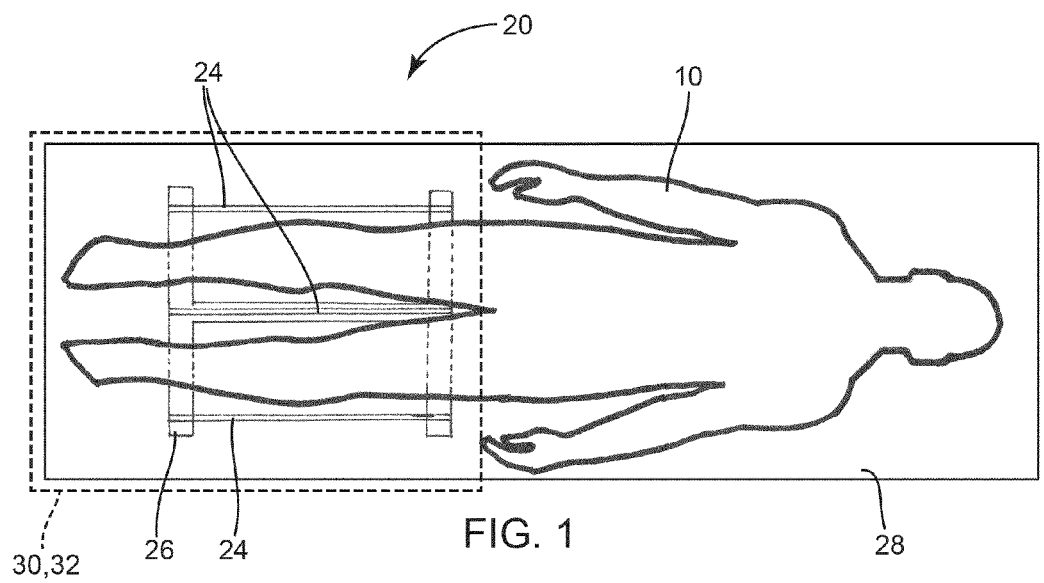
FIG. 1 is a top view of a radiation attenuation system positioned proximate the legs of a patient, according to an exemplary embodiment.

Referring to FIGS. 1 through 5, a radiation attenuation system 20 and components thereof are shown according to exemplary embodiments. Generally, radiation attenuation system 20 includes one or more radiation shields or barriers supported in a manner and at a position that may be useful in attenuating (e.g., blocking, reflecting, absorbing, etc.) primary beam radiation and/or secondary or scatter radiation generated during lateral radiographic imaging of an object (e.g., patient, etc.). For purposes of the present disclosure, the phrase "lateral radiographic imaging," unless expressly stated otherwise, is used broadly to refer to not only literal lateral imaging of an object (i.e., end-to-end wherein the primary radiation beam is emitted in a horizontal direction that is substantially parallel to a ground surface or a support surface for the object), but also partially lateral or oblique imaging of the object (i.e., wherein the primary radiation beam is emitted at an angle (e.g., 20, 30 or 40 degrees, etc.) relative to a ground surface or a support surface for the object). For example, lateral radiographic imaging need not be strictly horizontal or strictly in the coronal plane of the patient.

The radiation attenuation system 20 generally includes a plurality of radiation shields or barriers provided in the form of rigid panels (show, e.g., as plates 24). The panels are removably coupled to and held upright by a frame 26. The panels are received in slots formed in the frame and can be removed from the frame for storage. The radiation attenuation system 20 is configured to be a reusable device that may be utilized for multiple patients.

A wide array of medical procedures exist where radiological examinations are employed to obtain an image of the anatomy of a patient or portions thereof. For example, portions of a patient's anatomy may be irradiated during: (i) diagnostic procedures (e.g., Computed Tomography (CT) scanning, x-ray photography, or any other imaging procedure) allowing non-invasive investigation of anatomical regions of a patient (e.g., internal tissue, organs, etc.); or (ii) various invasive procedures, such as the fluoroscopic guidance and/or manipulation of instruments during surgical procedures (e.g., CT fluoroscopy, etc.).

To obtain an image through a radiological examination, a primary radiation beam (i.e., entrance radiation) is applied to the patient. Preferably, radiation is selectively focused on to those areas to be examined (i.e., target areas) to minimize the patient's overall radiation exposure. Typically, the target areas are irradiated directly without any obstruction or impairment provided between the primary radiation beam and the patient. Those areas above and/or below the target area that are not being examined (i.e., secondary areas) may be covered with a radiation barrier or shield to prevent and/or reduce radiation exposure for those areas. Such shields are formed of a radiation attenuating material (e.g., lead apron, radiation attenuating polymeric matrix, etc.) and may be placed directly upon the patient. According to an exemplary embodiment, the radiation attenuating material is a polymeric matrix charged with an attenuating filler. Examples of suitable radiation attenuation materials are disclosed in U.S. Pat. No. 4,938,233, entitled "Radiation Shield," and U.S. Pat. No. 6,674,087, entitled "Radiation Attenuation System," both of which are hereby incorporated by reference in their entireties.

It should be noted that for purposes of this disclosure, the term "coupled" is used broadly to mean the joining or combining of two or more members (e.g., portions, layers, materials, components, etc.) directly or indirectly to one another. Such joining or combining may be relatively stationary (e.g., fixed, etc.) in nature or movable (e.g., adjustable, etc.) in nature. Such joining or combining may be achieved with the two members or the two members and any additional intermediate members being integrally formed as a single unitary body with one another (e.g., one-piece, etc.) or with the two members or the two members and any additional intermediate member being attached to one another. Such joining or combining may be intended to be relatively permanent in nature or alternatively may be intended to be relatively detachable or removable in nature.

The radiation barriers are configured to protect one or more individuals present during a procedure (e.g., technicians, assistants, nurses, physicians, surgeons, etc.), referred to generally herein as medical personnel. One or more medical personnel are likely to be positioned near the patient during the procedure, and as such, are likely to be positioned close to the primary radiation beam (i.e., between the emitter and receiver) and/or an area likely to be exposed by scatter radiation. Medical personnel present during the radiographic imaging of the patient may also be susceptible to radiation exposure from the primary radiation beam (e.g., during a fluoroscopy procedure, etc.), but are more likely to be susceptible to radiation exposure from secondary or incidental scatter radiation. The radiation barriers protect against scatter radiation by absorbing at least a portion of the primary radiation beam and scatter radiation.

The frame 26 positions the radiation barriers in an upright orientation, forming a trough or channel with an open top into which a portion of the patient's body to be scanned (e.g., an arm or leg) may be received. The open top of the radiation attenuation system 20 provides medical personnel with access to an area of interest on the patient (e.g., target area, etc.). During a procedure, a radiographic visualization or imaging device (e.g., fluoroscope, etc.) will likely be positioned such that a radiation emitter of the device is located at a first end (e.g., inferior end) of the patient and that a corresponding radiation receiver of the device is located at an opposite second end (e.g., superior end). The panels act as radiation barriers positioned between the emitter and the receiver, parallel to the radiation beam, to limit stray radiation.

Figure 2:
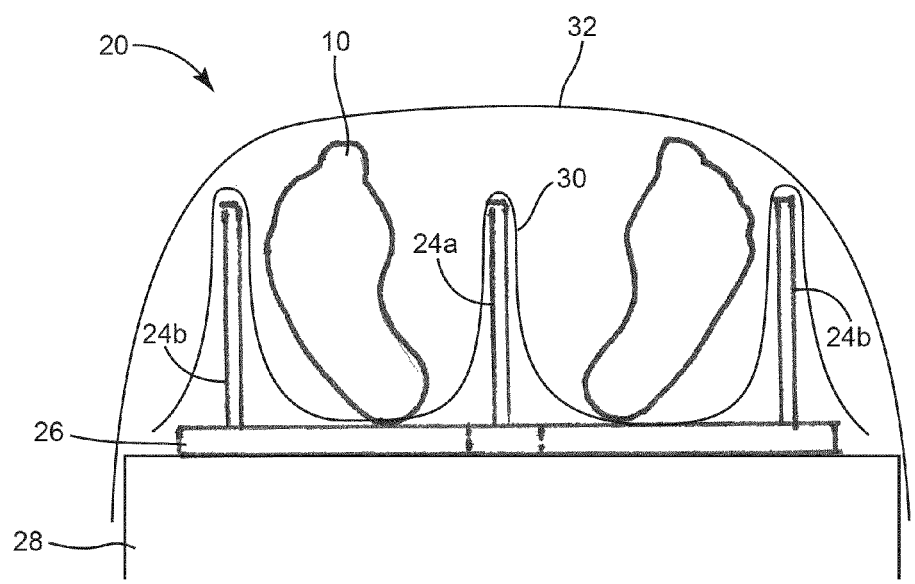
FIG. 2 is an end view of the radiation attenuation system of FIG. 1 positioned proximate the legs of a patient.

Referring to FIGS. 1-2, the radiation attenuation system 20 is shown according to an exemplary embodiment. The radiation attenuation system 20 is configured to receive a portion of a patient 10 during a medical procedure including lateral radiographic imaging. For example, according to an exemplary embodiment, the radiation attenuation system 20 is configured for use with the lower limbs of the patient 10. In other exemplary embodiments, the radiation attenuation system 20 may be configured for use with another portion of the patient 10, such as an upper limb, torso, head, etc. The radiation attenuation system 20 includes one or more upright plates 24 coupled to a frame 26 supported by a platform 28 (e.g., table, examination table, operating table, etc.) and positioned below the patient 10.

As shown, a sheet 30 may be provided between the patient 10 and the plates 24 and/or the frame 26. The sheet 30 serves as a lining between the patient 10 and the plates 24 and/or the frame 26 to limit the contact between the patient 10 and the plates 24 and the frame 26 thereby maintaining the cleanliness and/or hygiene of the radiation attenuation system 20. The radiation attenuation system 20 may further include a drape 32 that lies over the patient 10. The sheet 30 and the drape 32 may be formed from any suitable textile material, such as a woven or knit textile or a non-woven textile. The sheet 30 and the drape 32 may be formable (e.g., deformable), compliant, and/or relatively "stretchable" (e.g., elastic). The sheet 30 may be formed from a variety of fibers (e.g., cotton, paper, polyester, etc.) and may be configured to be disposable in whole or in part, thereby minimizing ancillary sources of contamination that may arise from multiple uses. In some embodiments, the sheet 30 and/or the drape 32 may be formed at least partially of a radiation attenuating material.

The radiation attenuation system 20 may be used regardless of the position of the patient. For example, the patient may be provided in a supine position wherein the patient is positioned on his or her back with the legs of the patient being straight or bent, a prone position wherein the patient is positioned face down, and/or a lateral position wherein the patient is positioned on one side. When the emitter and receiver are placed above and below the patient (e.g., in substantially vertical alignment, above and below the examination table, etc.), the beam may pass substantially transverse to a longitudinal axis of the trough, and radiographic images of the coronal or sagittal planes may be obtained. Accordingly, with a patient in the supine or prone positions, the primary radiation beam may pass towards the front or back of the patient, and with a patient in the lateral position, the primary radiation beam may pass through the side of the patient. It is contemplated that the emitter and receiver may be oriented longitudinally with respect to the trough such that the beam may pass substantially along a superior-inferior axis so as to obtain radiographic images of the transverse plane.

Referring to FIG. 2, the in an situation where the emitter is located below the platform 28 and emits as primary beam upward through the patient, the beam will begin to scatter when it makes first contact with the patient mass (e.g., the back of the patient's leg). Radiation scattered downward (e.g., low flying scatter) may be reflected by the medical personnel's apron. Lateral or upward scatter is attenuated and/or reflected up through the top of the trough. According to one embodiment, the height of the plates 24 is such that a radiation shadow (e.g., umbra, penumbra, etc.) is formed to the side of the platform 28, which substantially shields nearby medical personnel. According to an exemplary embodiment, the height of the plates 24 is such that a radiation shadow is formed to the side of the platform 28 such that medical personnel standing near the platform are within an umbra of the plates 24. According to another embodiment, the cross-section of the trough is configured such that radiation escaping the top of the trough to the side of the platform on which medical personnel are standing passes over the top of the medical personnel.

The plates 24 are positioned proximate the area of interest being scanned such that they attenuate the scatter radiation. According to an exemplary embodiment, the plates 24 are rigid transparent panels. In one embodiment, the plates 24 may be formed of an acrylic lead material (e.g., leaded acrylic, lead acrylic, etc.). In another embodiment, the plates 24 may be formed of a leaded glass material. In still other embodiments, the plates 24 may be formed of any appropriate radiation attenuation material including, but not limited to, bismuth, barium, lead, tungsten, antimony, copper tin, aluminum, iron, iodine, cadmium, mercury, silver, nickel, zinc, thallium, tantalum, tellurium, and uranium. Anyone of the aforementioned radiation attenuation materials alone or in a combination of two or more of the radiation attenuation materials may provide the desired level of radiation attenuation. According to one embodiment, the plates 24 may be formed of a medium having a radiation attenuation material suspended therein. According to an exemplary embodiment, the radiation attenuating material is a polymeric matrix charged with an attenuating filler. It should be noted that the radiation attenuating member is not limited to such radiation attenuating materials, and according to the various alternative embodiments, may be formed of any suitable radiation attenuating material including more conventional attenuating materials (e.g., lead-based materials, etc.).

The radiation attenuation factor of the plates 24 may vary depending upon the intended application of radiation attenuation system 20, for example, attenuating direct or scattered radiation. Further, higher powered beams (kVp) and larger patients tend to cause greater scattering of the radiation. According to one exemplary embodiment, the radiation attenuating member may have a radiation attenuation factor of nearly 100 percent (%) with reference to a 60 kVp x-ray beam. According to another embodiment, the radiation attenuating member may have a radiation attenuation factor of approximately 30 percent (%) with reference to a 90 kVp x-ray beam. The plates 24 may also at least partially attenuate gamma rays.

According to an exemplary embodiment, the plates 24 have a thickness of between 4 mm and 24 mm. According to another embodiment, each plate 24 has a thickness of between 4 mm and 18 mm. According to a preferred embodiment, the plates 24 have a thickness of between 6 mm and 18 mm. According to a particularly preferred embodiment, the plates 24 have a thickness of between 8 mm and 12 mm.

According to an exemplary embodiment, the plates 24 are configured to attenuate the radiation for a peripheral procedure involving the legs of the patient 10. In one embodiment, the radiation attenuation system 20 includes an inner plate 24a positioned between the legs of the patient 10 and a pair of outer plates 24b positioned along the outside of either of the legs of the patient 10. According to an exemplary embodiment, the plates 24 have a height of between approximately 8 in. and 14 in.

Figure 3:
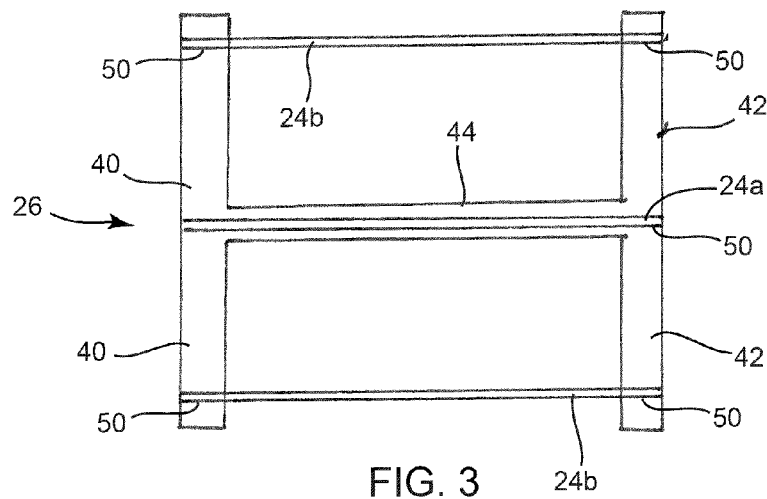
FIG. 3 is a top view of the radiation attenuation system of FIG. 1.
Figure 4:
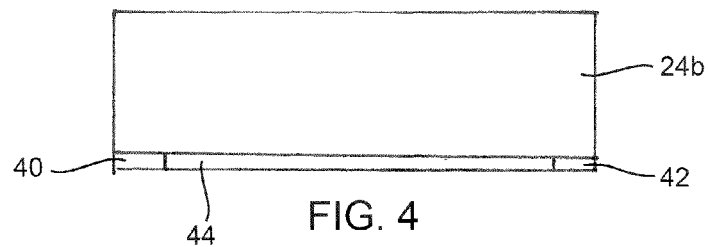
FIG. 4 is a side view of the radiation attenuation system of FIG. 1.

The plates 24 are held in an upright orientation by the frame 26. Referring to FIGS. 3-4, the frame 26 is a low-profile structure that is provided between the patient 10 and a supporting structure, such as the platform 28. According to an exemplary embodiment, the frame 26 is I-shaped body with a first end portion including a pair of first arms 40 (e.g., superior end portion, proximal end portion, etc.) and a second end portion including a pair of second arms 42 (e.g., inferior end portion, distal end portion, etc.). As shown in FIG. 1, the frame 26 may lie between the buttocks and the heels of the patient 10 in the supine position. The first arms 40 and the second arms 42 are coupled together by a connecting portion 44 (e.g., rib, rail, leg, etc.) shown to be perpendicular to the arms 40, 42. According to an exemplary embodiment, the frame 26 includes a single connecting portion 44 extending between the arms 40, 42 and under a gap between the legs of the patient 10. In other exemplary embodiments, the frame 26 may include additional connecting portions, such as connecting portions extending from the distal ends of the arms 40 and 42. In still other exemplary embodiments, the arms 40, 42 may be coupled together by a connecting portion in the form of a panel that extends along the entire length of the arms 40, 42.

The length of the connecting portion 44 of the frame 26 may vary depending on the desired length of the radiation attenuation system 20. Any number of radiation attenuation systems 20 of various lengths (e.g., having plates 24 and frames 26 with various lengths) may be provided to be used with patients of various sizes.

Due to the placement of the frame 26 between the buttocks and the heels of the patient 10 and the relatively low profile of the frame 26, one or more of the elements of the frame 26 (e.g., the first arms 40, the second arms 42, and the connecting portion 44) may have a rectangular cross-section without causing undue discomfort for the patient. In another exemplary embodiment, one or more of the elements of the frame 26 may have rounded edges. In another exemplary embodiment, the first arms 40 and/or the second arms 42 may include hollows or cutouts configured to comfortably receive the legs of the patient 10.

The frame 26 includes a multitude of slots 50 configured to receive the plates 24. The slots 50 are formed are formed in the arms 40 and 42, with the slots 50 on the first arms 40 forming an array that is aligned with corresponding array of slots 50 on the second arms 42. The connecting portion 44 may define a slot 50 (e.g., a longitudinal slot) running along the length of the connecting portion 44 (e.g., to receive the inner plate 24a). The slots 50 have a width and a depth to facilitate the assembly and use of the radiation attenuation system 20 with minimal components and no additional tools. According to an exemplary embodiment, the width of the slots 50 is equal to or less than the thickness of the plates 24, such that the plates 24 can be inserted (e.g., slid) into the slots 50 by hand. The plates 24 may be held loosely in the slots 50 or may be held in the slots 50 with an interference fit between the plates 24 and the frame 26. According to an exemplary embodiment, the depth of the slots 50 is great enough that the plates 24 may be supported by the frame 26 in an upright orientation without additional support. The slots 50 may have a depth that is less than the height of the frame 26 such that the slots 50 extend only part of the way through the frame 26 or may extend through the entire frame 26 and divide the frame 26 into separate portions that are coupled together, for example, as shown in FIG. 6. In some embodiments, the frame 26 may include slots 50 of varying widths to accommodate plates 24 having varying thicknesses.

The frame 26 is a relatively lightweight structure formed of a material that need not be opaque to the radiation utilized in the procedure. According to an exemplary embodiment, the frame 26 is molded from a semi-rigid, relatively resilient material, such as a high-density polypropylene foam, high density polyethylene, HDPE foam, rubber, etc. In other exemplary embodiments, the frame 26 may be formed from a more rigid material, such as acrylic, glass, etc. When formed from a resilient material, the slots 50 may, in a relaxed state, have a width that is less than the thickness of the plates 24, and the plates 24 cause the portions of the frame 26 defining the slots 50 to deform such that the plates 24 are held in place with an interference fit. Although not required, the frame 26 is preferably formed from a radiotranslucent material so as not to interfere with the imaging of the patient. In other embodiments, the frame 26 may be formed from multiple materials. For example, the frame 26 may include a main body formed of a relatively rigid material and inserts formed of a relatively resilient material in which the slots 50 are formed. The multiple materials may be formed with a two-shot molding process or may be formed separately and coupled together, such as with an adhesive. In other embodiments, the top of the frame may include a layer of softer, deformable material to increase the comfort of the patient.

Figure 5:
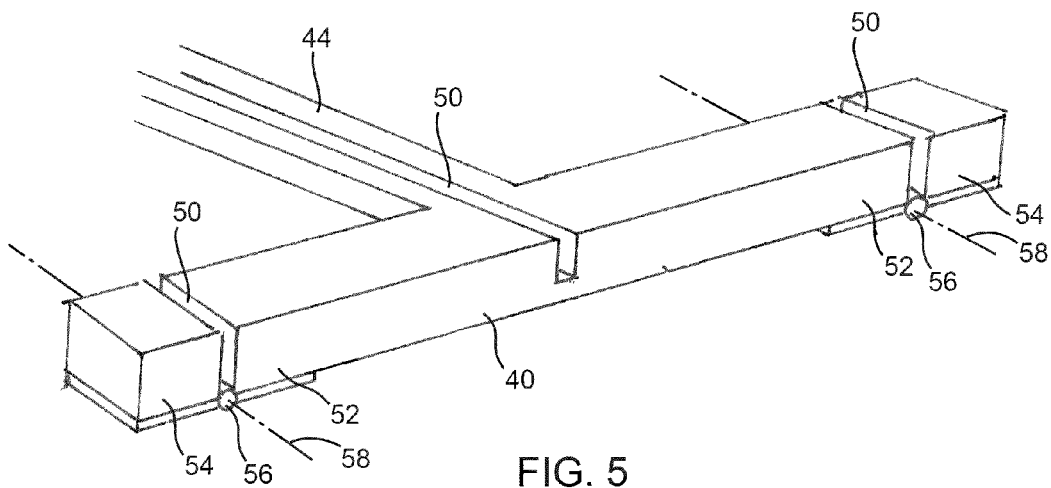
FIG. 5 is a perspective view of an end of the radiation attenuation system of FIG. 1 with the radiation shields removed.

Referring now to FIG. 5, in one embodiment, the slots 50 may extend through the entire height of the arms 40 (and/or of the arms 42), and divide the arms 40 into an inner portion 52 and an outer portion 54. The inner portion 52 is coupled to the outer portion 54 with a hinge member 56 that is configured to allow the outer portion 54 to pivot relative to the inner portion 52 about an axis 58, thereby varying the width of the slot 50 to facilitate the insertion of the plate 24 into the slot 50. According to one exemplary embodiment, the hinge member 56 is a pinned hinge coupled to the bottom surface of the arm 40. In other exemplary embodiments, the hinge member 56 may be another type of hinge, such as a flexible sheet coupled to the bottom surface of the arm 40 or a living hinge integrally formed with the inner portion 52 and the outer portion 54 of the arm 40. The slot 50 may be widened, for example, by lifting the frame 26 off of the platform 28 and allowing the outer portion 54 to pivot downward. The plate 24 may then be positioned in the slot 50 and the slot 50 narrowed by lowering the frame 26 onto the platform 28, forcing the outer portion 54 to pivot upward. The hinge member 56 may be pinned or otherwise held in place with a locking mechanism, such as when the outer portion 54 is pivot upward and the slot 50 is narrowed. In other embodiments, the hinge member 56 may lack a locking mechanism and the plate 24 may be retained in the slot 50 and the outer portion 54 may be held in position by the weight of the patient forcing the frame 26 against the platform 28.

Although the radiation attenuation system 20 is shown as being an I-shaped structure configured to accommodate two limbs, in another embodiment, the radiation attenuation system 20 may be configured to accommodate a single limb. Such a radiation attenuation system 20 may include a frame 26 with a connecting portion 44 disposed on one or both sides of the radiation attenuation system 20 or running generally along the center of the radiation attenuation system 20 (e.g., under the limb). It is further contemplated that the radiation attenuation system 20 described above may be used with less than the full accompaniment of plates 24. According to various embodiments, plate 24a, one of plates 24b, both of plates 24b, or plate 24a and one of plates 24b may be removed from the frame 26 to create the desired attenuation scheme for the radiological examination.

One or more of the components of radiation attenuation system 20 are generally non-toxic, recyclable, and/or biodegradable. According to an alternative embodiment, one or more of the components of radiation attenuation system 20 may be reusable. According to a preferred embodiment, one or more of the components of radiation attenuation system 20 may be sterilized between uses to minimize the likelihood of bacteriological or virus contamination. Sterilization may be performed in any convenient manner, including gas sterilization and irradiation sterilization.

It is important to note that the construction and arrangement of the elements of the radiation attenuation system as shown in the illustrated embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, or the length or width of the structures and/or members or connectors or other elements of the system may be varied. It should be noted that the elements and/or assemblies of the system may be constructed from any of a wide variety of materials that provide sufficient strength or durability, in any of a wide variety of colors, textures and combinations. For example, the radiation attenuation material may be a relatively flexible material, or alternatively, may be a relatively rigid material. Further, drape 32 may not include the fenestration area if drape 32 is not going to be used for invasive procedures. Further, while lateral radiographic imaging is used above with reference to a primary radiation beam that is generally parallel to a patient table, the angle at which the primary radiation beam may emitted relative to a patient table during lateral radiographic imaging may be up to approximately 45 degrees (or any other degree of obliquity) relative to the patient table. Accordingly, all such modifications are intended to be included within the scope of the present inventions. Other substitutions, modifications, changes and omissions may be made in the design, operating conditions and arrangement of the preferred and other exemplary embodiments without departing from the spirit of the present inventions.

What is claimed is:

1. A radiation attenuation system, comprising:
   a first shield panel formed of a first radiation attenuating material;
   a second shield panel formed of a second radiation attenuating material; and
   a frame disposed below the first shield panel and the second shield panel, the frame comprising:
      a first end portion defining a first array of slots; and
      a second end portion defining a second array of slots; and
   wherein the first array of slots and the second array of slots are configured to receive an end portion of the first shield panel and an end portion of the second shield panel such that the second shield panel is spaced apart from the first shield panel to form a first trough sized to fit a limb of a patient.

2. The radiation attenuation system of claim 1, wherein the first radiation attenuating material and the second radiation attenuating material both comprise at least one of acrylic lead or leaded glass.

3. The radiation attenuation system of claim 2, wherein the first shield panel and the second shield panel each have a thickness of between 4 mm and 18 mm.

4. The radiation attenuation system of claim 1, further comprising a connecting portion extending between the first end portion and the second end portion.

5. The radiation attenuation system of claim 4, wherein the frame comprises an I-shaped structure configured to receive both legs of the patient.

6. The radiation attenuation system of claim 1, further comprising:
   a third shield panel;
   wherein the first array of slots and the second array of slots are configured to receive an end portion of the third shield panel such that the third shield panel is spaced apart from the first shield panel to form a second trough sized to fit a limb of the patient.

7. The radiation attenuation system of claim 6, further comprising a connecting portion extending between the first end portion and the second end portion;
   wherein the connecting portion defines a longitudinal slot extending between the first array of slots and the second array of slots; the first shield panel being received in the longitudinal slot.

8. The radiation attenuation system of claim 1, wherein the first end portion comprises a first hinged outer portion; the first hinged outer portion defining a first slot; and wherein the second end portion comprises a second hinged outer portion; the second hinged outer portion defining a second slot.

9. The radiation attenuation system of claim 1, wherein the frame holds the first shield panel and the second shield panel upright by receiving the end portion of the first shield panel and the end portion of the second shield panel.

10. A radiation attenuation system for the scanning of a leg of a patient, comprising:
    a first shield panel;
    a second shield panel;
    a third shield panel; and
    a frame disposed below the first shield panel, the second shield panel, and the third shield panel, the frame comprising:
       a connecting portion extending from a first end to a second end;
       at least one first arm defining a first array of slots and extending outward from the connecting portion between the first end and the second end; and
       at least one second arm defining a second array of slots and extending outward from the connecting portion between the at least one first arm and the second end;
    wherein the first array of slots and the second array of slots are configured to receive an end portion of the first shield panel, an end portion of the second shield panel, and an end portion of the third shield panel such that the second shield panel and the third shield panel are spaced apart from the first shield panel to form a pair of troughs sized to fit the legs of the patient.

11. The radiation attenuation system of claim 10, wherein the first shield panel and the second shield panel comprise at least one of acrylic lead or leaded glass.

12. The radiation attenuation system of claim 10, wherein the connecting portion extends substantially parallel to the leg of the patient and defines a longitudinal slot extending between the first array of slots and the second array of slots; the first shield panel being received in the longitudinal slot.

13. The radiation attenuation system of claim 10, wherein the frame comprises high density polypropylene foam.

14. The radiation attenuation system of claim 10, wherein the at least one first arm comprises an inner portion and an outer portion coupled to the inner portion by a hinged member and defining a space between the inner portion and the outer portion, the space between the inner portion and the outer portion defining a first slot of the first array of slots.

15. An apparatus for attenuating radiation scattered from a patient undergoing radiological examination on a table, comprising:
    a frame configured to be supported by the table; and
    a first shield panel formed of a radiation attenuating material and supported by a first portion of the frame on an end portion of the first shield panel;
    wherein the first shield panel at least partly defines a trough configured to receive a limb of the patient and attenuates radiation scattered from the patient.

16. The apparatus of claim 15, comprising a second shield panel formed of the radiation attenuating material and supported by a second portion of the frame on an end portion of the second shield panel;
    wherein the first shield panel, the second shield panel, and the frame at least partly define the trough.

17. The apparatus of claim 16, wherein the frame comprises a third portion located between the first portion and the second portion, the third portion including a cutout configured to comfortably receive the limb of the patient.

18. The apparatus of claim 15, wherein the radiation attenuating material comprises a medium having an attenuating material suspended therein.

19. The apparatus of claim 18, wherein the radiation attenuating material comprises at least one of acrylic lead or leaded glass.

20. The apparatus of claim 18, wherein the frame comprises a semi-rigid, radiotranslucent material.

\* \* \* \* \*